United States Patent [19]

Nowotnik et al.

[11] Patent Number: 5,651,954

[45] Date of Patent: Jul. 29, 1997

[54] METHOD OF USING HYDRAZONE CONTAINING LIGANDS AND METAL COMPLEXES THEREOF

[75] Inventors: David P. Nowotnik, Flemington; Palaniappa Nanjappan, Dayton, both of N.J.

[73] Assignee: Bracco International B.V., Amsterdam, Netherlands

[21] Appl. No.: 473,563

[22] Filed: Jun. 6, 1995

Related U.S. Application Data

[62] Division of Ser. No. 180,260, Jan. 12, 1994, abandoned.

[51] Int. Cl.$^6$ .................................................. A61K 51/04
[52] U.S. Cl. ........................................................ 424/1.65
[58] Field of Search ............................................ 424/1.65

[56] References Cited

U.S. PATENT DOCUMENTS

| | | | |
|---|---|---|---|
| 3,369,121 | 2/1968 | Bruno et al. | 250/106 |
| 3,920,995 | 11/1975 | Czaplinski et al. | 250/432 |
| 4,615,876 | 10/1986 | Troutner et al. | 424/1.1 |
| 4,789,736 | 12/1988 | Canning et al. | 534/14 |
| 4,818,813 | 4/1989 | Nowotnik et al. | 534/14 |
| 4,871,836 | 10/1989 | Francesconi | 534/10 |
| 4,895,960 | 1/1990 | Duetsch | 548/950 |
| 5,026,829 | 6/1991 | Deutsch | 534/14 |
| 5,101,041 | 3/1992 | Troutner et al. | 548/518 |
| 5,116,598 | 5/1992 | Nosco | 424/1.1 |
| 5,200,541 | 4/1993 | Thami | 556/110 |
| 5,384,108 | 1/1995 | Rajagopalan | 424/9 |
| 5,387,692 | 2/1995 | Riley et al. | 548/313.7 |
| 5,506,345 | 4/1996 | Riley et al. | 534/14 |
| 5,589,576 | 12/1996 | Archer et al. | 534/14 |

FOREIGN PATENT DOCUMENTS

| | | |
|---|---|---|
| 61290/90 | 3/1991 | Australia. |
| 12147/92 | 9/1992 | Australia. |
| 12148/92 | 9/1992 | Australia. |
| 2023595 | 3/1991 | Canada. |
| 2081637 | 10/1992 | Canada. |
| 123504 | 10/1984 | European Pat. Off.. |
| 179608 | 4/1986 | European Pat. Off.. |
| 194843 | 9/1986 | European Pat. Off.. |
| 417870 | 3/1991 | European Pat. Off.. |
| 441491 | 8/1991 | European Pat. Off.. |
| 544412 | 6/1993 | European Pat. Off.. |
| 92/07860 | 5/1992 | WIPO. |
| 93/02045 | 2/1993 | WIPO. |
| 94/08949 | 4/1994 | WIPO. |

OTHER PUBLICATIONS

English translation of Svetkin et al., Zh. Obshchei Khimii, 41(11), pp. 2553–2555 (1971).
Kotyk et. al., "Biophysical Chemistry of Membrane Functions", Chichester, UK. Publ. John Wiley & Sons, 1988.
Volkert, W.A. et al., "$^{99m}$Tc–propylene amine oxime (99mTc–PnAO); a potential brain radiopharmaceutical", Eur. J. Nucl. Med., 9, pp. 511–516 (1984).
Jurisson et al., "Synthesis, Characterization, and X–ray Structural Determination of Technetium (V)–Oxo–Tetradentate Amine Oxime Complexes", Inorg. Chm., 25, pp. 543–549 (1986).
Ding et al., "Review and Prospectives of Brain Radiopharmaceuticals", Nucl. Sci. J., 29(5), pp. 341–348 (1992).
Moody et al., J. Chem. Soc. Perkin Trans. 1, (1), pp. 18–24 (1972).
Hook et al., Anti–Cancer Drug Res., 4(3), pp. 173–190 (1989).
Vassian et al., "Aromatization of an Aliphatic Amine Oxime Nickel (II) Complex by Molecular Oxygen", Inorg. Chemistry, vol. 6, No. 11, pp. 2043–2046 (1967).
Murmann et al., "An Unsymmetrical *trans*Dinitrocobalt (III) Complex. A Crystal Structure Determination", Inorg. Chem., vol. 12, No. 11, pp. 2625–2631 (1973).
March, Advanced Organic Chemistry, p. 804 (1985).

*Primary Examiner*—John Kight
*Assistant Examiner*—Lara Chapman Kelley
*Attorney, Agent, or Firm*—George P. Hoare; Donald L. Rhoads

[57] ABSTRACT

Novel compounds of the formula

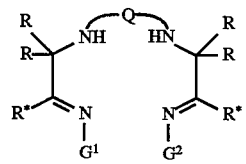

where $G^1$ and $G^2$ are each independently —OH or —N(R$^2$)$_2$, provided that at least one of $G^1$ and $G^2$ is —N(R$^2$)$_2$, where each R$^2$ is independently hydrogen, alkyl, aryl, acyl or —(A)$_p$—R$^a$ and the other variables are as defined in the specification and claims, and novel complexes of these compounds with metals are useful in diagnostic and therapeutic methods.

6 Claims, No Drawings

METHOD OF USING HYDRAZONE CONTAINING LIGANDS AND METAL COMPLEXES THEREOF

This is a divisional of application Ser. No. 08/180,260, filed Jan. 12, 1994 now abandoned.

FIELD OF THE INVENTION

The present invention relates to novel compounds and to novel complexes of these compounds with metals. The novel compounds and complexes of the present invention find utility in diagnostic and therapeutic methods.

BACKGROUND OF THE INVENTION

Metal complexes, such as those containing radioactive metals, are finding increasing use as diagnostic and therapeutic agents. Of particular interest are those complexes containing bioactive moieties capable of being selectively taken up at a desired site to facilitate evaluation or treatment of a subject.

The present invention addresses the need in the art for such complexes and the ligands from which they are prepared.

SUMMARY OF THE INVENTION

The present invention provides novel compounds, also referred to herein as ligands, of the following formula I:

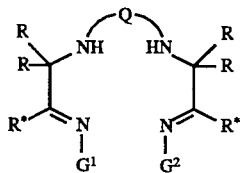

where

Q is the group $-(C(RR))_{m1}-(Y_1)_n-(C(RR))_{m2}-(Y^2-(C(RR))_{m3})_{n1}$, $y^1$ and $y^2$ are each independently $-NR-$, $-O-$, $-S-$, $-SO-$, $-SO_2-$ or $-Se-$; n and n1 are each independently 0 or 1; and m1, m2 and m3 are each independently 0 or an integer from 1 to 4; provided that m1 and m2 are not both 0, that m1+m2+n+n1 is less than 6 and that a carbon atom bearing an R group is not directly bonded to more than one heteroatom;

each R and R* group is independently:
 (i) $R^1$;
 (ii) alkoxy;
 (iii) hydroxy;
 (iv) halogen, especially fluoro;
 (v) haloalkyl;
 (vi) $-OR^1$;
 (vii) $-C(O)-OR^1$;
 (viii) $-C(O)-N(R^1)_2$;
 (ix) $-N(R^1)_2-$;
 (x) $-N(R^1)-COR^1$;
 (xi) $-alkyl-C(O)-OR^1$;
 (xii) $-alkyl-C(O)-N(R^1)_2$;
 (xiii) $-alkyl-N(R^1)_2-$;
 (xiv) $-alkyl-N(R^1)-COR^1$;
 (xv) $-aryl-C(O)-OR^1$;
 (xvi) $-aryl-C(O)-N(R^1)_2$;
 (xvii) $-aryl-N(R^1)_2-$;
 (xviii) $-aryl-N(R^1)-COR^1$;
 (xix) nitrile;
 (xx) acyl;
 (xxi) acyloxy;
 (xxii) heterocyclo;
 (xxiii) hydroxyalkyl;
 (xxiv) alkoxyalkyl;
 (xxv) hydroxyaryl;
 (xxvi) arylalkyl;
 (xxvii) $-SO_2-R_1$;
 (xxviii) $-alkyl-SO_2-R^1$;
 (xxix) $-(A)_p-R^a$, where A is a linking group, p is 0 or a positive integer, and $R^a$ is a bioactive moiety or a reactive group capable of forming a covalent bond to a bioactive moiety; or
 (xxx) two of the groups, taken together with one or more atoms to which they are bonded, form a saturated or unsaturated, spiro or fused, carbocyclic (such as fused 1,2-phenyl) or heterocyclic ring which may be unsubstituted or substituted by one or more groups selected from the groups (i) to (xix) above;

each $R^1$ is independently hydrogen, alkyl, alkenyl, alkynyl or aryl; and $G^1$ and $G^2$ are each independently $-OH$ or $-N(R^2)_2$, provided that at least one of $G^1$ or $G^2$ is $-N(R^2)_2$, where each $R^2$ is independently hydrogen, alkyl, aryl, acyl or $-(A)_p-R^a$.

The present invention also provides complexes of the aforementioned compounds of the formula I with metals, preferably rhenium or technetium, and the use of these complexes in diagnostic and therapeutic methods. Further provided by the present invention are kits for preparing the metal complexes of the present invention.

In certain embodiments, the present invention provides complexes, without a specific bioactive moiety, that localize selectively in an organ or organ system and may be useful for heart, brain, hepatobiliary or other organ imaging. In other embodiments, the present invention provides complexes containing bioactive moieties, such as receptor or hypoxia-localizing moieties, which retain the biochemical behavior and affinity of the free moieties and which are capable of rapidly providing increased amounts of a desired radionuclide selectively to targeted areas. Certain complexes of the invention may be labeled at ambient temperature with suitable, easy-to-use radionuclides; and some complexes may be membrane permeable, allowing intracellular delivery.

DESCRIPTION OF THE INVENTION

The present invention is described further as follows.

Definitions

Listed below are definitions of terms used to describe the present invention. These definitions apply to the terms as they are used throughout the specification unless otherwise indicated.

The terms "alkyl" or "alkl", as used herein alone or as part of another group, denote optionally substituted, straight and branched chain saturated hydrocarbon groups, preferably having 1 to 12 carbons in the normal chain. Most preferably, these groups are lower alkyl groups. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents include one or more of the following groups: halo, alkoxy, alkylthio, alkenyl, alkynyl, aryl, cycloalkyl, cycloalkenyl, hydroxy, carboxyl (—COOH), amino, alkylamino, dialkylamino, formyl, alkylcarbonyloxy, alkylcarbonyl, heterocyclo or thiol (—SH). Preferred alkyl groups are unsubstituted alkyl, haloalkyl, arylalkyl, aminoalkyl, alkylaminoalkyl, dialkylaminoalkyl, alkoxyalkyl, aryloxyalkyl and hydroxyalkyl groups.

The terms "lower alkyl" or "lower alk", as used herein, denote optionally substituted groups as described above for alkyl but having only 1 to 4 carbon atoms in the normal chain.

The terms "alkoxy" or "alkylthio" denote an alkyl group as described above bonded through an oxygen linkage (—O—) or a sulfur linkage (—S—), respectively. The term "alkylcarbonyl", as used herein, denotes an alkyl group bonded through a carbonyl group. The term "alkylcarbonyloxy", as used herein, denotes an alkyl group bonded through a carbonyl group which is, in turn, bonded through an oxygen linkage.

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted alkenyl groups include ethenyl, propenyl, butenyl, pentenyl, hexenyl, heptenyl, octenyl, nonenyl, decenyl and the like. Exemplary substituents include one or more alkyl groups as described above, and/or one or more groups described above as alkyl substituents.

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted alkynyl groups include ethynyl, propynyl, butynyl, pentynyl, hexynyl, heptynyl, octynyl, nonynyl, decynyl and the like. Exemplary substituents include one or more alkyl groups as described above, and/or one or more groups described above as alkyl substituents.

The term "cycloalkyl", as used herein alone or as part of another group, denotes optionally substituted, saturated cyclic hydrocarbon ring systems, preferably containing 1 to 3 rings and 3 to 7 carbons per ring. Exemplary unsubstituted cycloalkyl groups include cyclopropyl, cyclobutyl, cyclopentyl, cyclohexyl, cycloheptyl, cyclooctyl, cyclodecyl, cyclododecyl and adamantyl. Exemplary substituents include one or more alkyl groups as described above, and/or one or more groups described above as alkyl substituents.

The term "cycloalkenyl", as used herein alone or as part of another group, denotes such optionally substituted groups as described above for cycloalkyl, further containing at least one carbon to carbon double bond forming a partially unsaturated ring.

The term "aryl", as used herein alone or as part of another group, denote optionally substituted, homocyclic aromatic groups, preferably containing 1 or 2 rings and 6 to 12 ring carbons. Exemplary unsubstituted aryl groups include phenyl, biphenyl and naphthyl. Exemplary substituents include one or more, preferably three or fewer, nitro groups, alkyl groups as described above and/or groups described above as alkyl substituents. Preferred aryl groups are unsubstituted aryl and hydroxyaryl.

The term "carbocyclic", as used herein alone or as part of another group, denotes optionally substituted saturated, partially unsaturated or aromatic homocyclic hydrocarbon ring systems such as the cycloalkyl, cycloalkenyl or aryl groups described above.

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclic group may, for example, have 1 or 2 oxygen atoms, 1 or 2 sulfur atoms, and/or 1 to 4 nitrogen atoms in the ring. Each heterocyclic group may be bonded through any carbon or heteroatom of the ring system. Preferred groups include those of the following formula, which may be bonded through any atom of the ring system:

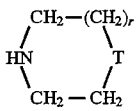

where r is 0 or 1 and T is —O—, —S—, —N—$R^3$ or —CH—$R^3$ where $R^3$ is hydrogen, alkyl, aryl or arylalkyl. Exemplary heterocyclic groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, morpholinyl, piperazinyl, 4-alkylpiperazinyl, 4-alkylpiperidinyl, 3-alkylpyrrolidinyl, oxazolyl, pyrazolyl, thiophenyl, pyridazinyl, thiazolyl, triazolyl, pyrimidinyl, 1,4-dioxanyl, benzoxadiazolyl and benzofurazanyl. Exemplary substituents include one or more alkyl groups as described above and/or one or more groups described above as alkyl substituents.

The terms "halogen" and "halo", as used herein alone or as part of another group, denote chlorine, bromine, fluorine and iodine.

The term "acyl", as used herein alone or as part of another group, denotes the moiety formed by removal of the hydroxyl group from the group —COOH of an organic carboxylic acid. Exemplary acyl groups include alkylcarbonyl, arylcarbonyl or carbocyclo- or heterocyclocarbonyl. The term "acyloxy", as used herein alone or as part of another group, denotes an acyl group as described above bonded through an oxygen linkage (—O—).

For the above optionally substituted groups, reference to a specific substituent may be made without excluding the presence of other substituents. Thus, for example, "hydroxyalkyl" is a straight or branched chain saturated hydrocarbon group bearing at least one hydromy substituent and, optionally, one or more additional substituents.

The expression "thiol protecting group", as used herein, denotes a group which may be cleaved from sulfur to yield a thiol group without destruction of the remainder of the molecule.

The expressions "bioactive group" and "bioactive moiety", as used herein, denote a group which is capable of functioning as a metabolic substrate, catalyst or inhibitor, or is capable of being preferentially taken up at a selected site of a subject, such as by possessing an affinity for a specific receptor.

The term "linking group", as used herein, denotes a group which, alone or together with one or more other groups, covalently bonds a bioactive group to the remainder of a compound of the formula I of the present invention.

The various substituents of the ligands of the present invention may be chosen to form stable compounds.

Compounds of the Formula I

The compounds of the formula I of the present invention may be prepared by methods such as those illustrated in, or analogous to, the following Reaction Schemes and in the Examples herein.

Reaction Schemes
Preparation of Compounds of the Formula I

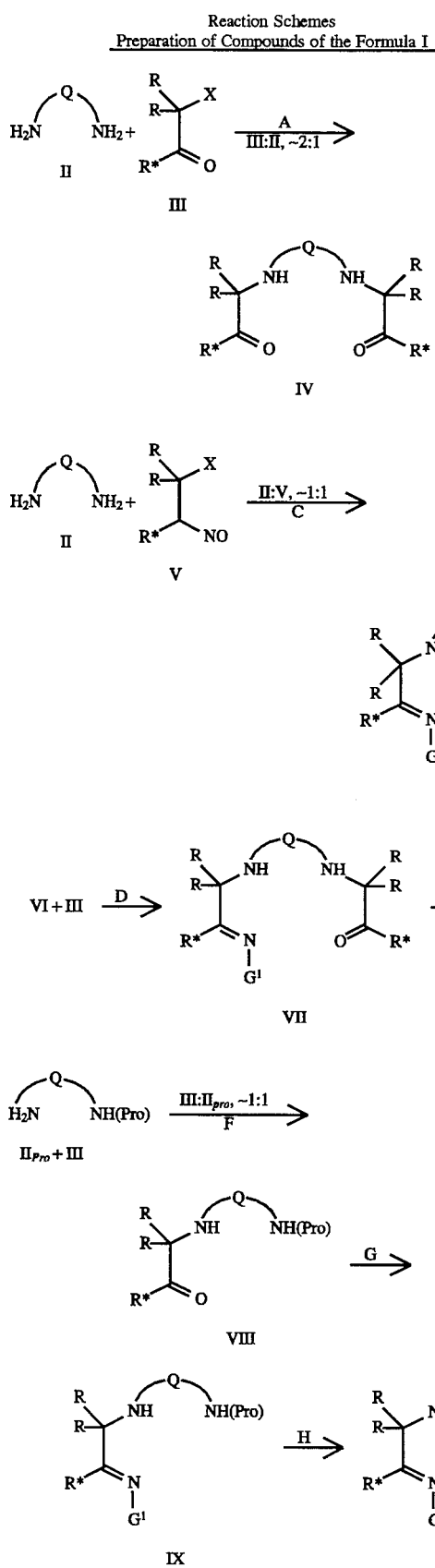

-continued
Reaction Schemes
Preparation of Compounds of the Formula I

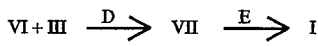

The above reaction schemes illustrate general methods for the preparation of compounds of the formula I.

According to the Reaction Scheme as shown in reaction A, a compound of the formula II may be contacted with approximately two or more molar equivalents of a haloketone III (where X is halogen) to form the diketone IV. A compound of the formula I may then be prepared in reaction B by conversion of the keto groups of the compound IV to hydrazone groups by methods such as treatment with a substituted hydrazine.

Alternatively, as shown in reaction C, a compound of the formula II may be contacted with an approximately equimolar amount of a compound of the formula V where X is halogen (preferably chloro), preferably in the presence of a tertiary amine such as diisopropylethylamine, to provide a compound of the formula VI. The compound of the formula VI may then be contacted in reaction D with a haloketone III to form a compound of the formula VII. The keto group of the compound of the formula VII may then be converted in reaction E to a hydrazone group by a method such as that described above for reaction B to form a compound of the formula I.

As the compounds of the formula II possess two terminal groups, it may be desirable to protect one of these groups to obtain preferential reaction through the unprotected amino group. Thus, compounds of the formula $II_{Pro}$ may be employed in another alternative method. As shown in reaction F, compounds of the formulae IIpro and III are contacted in an approximately equimolar ratio to form a monoketone of the formula VIII. The keto group of the compound VIII may be converted in reaction G to a hydrazone group by a method such as that described above for reaction B to form a compound of the formula IX. The compound of the formula IX is deprotected in reaction H to form a compound of the formula VI for further reaction. The latter compound may then be contacted with a haloketone of the formula III to yield a compound of the formula VII, and reaction E conducted yield a compound of the formula I as described above.

(Compounds of the formula III may be obtained by methods such as those described by Pfleiderer et al., Liebigs Ann. Chem., 99, 3008 (1966).)

Additionally, compounds of the formula I may be prepared where any R group can be readily incorporated into the ligand in the last reaction step by reacting a monooxime with a hydrazine that bears the desired R group. This is of particular advantage when the R group is hard to synthesize or is so labile that it might not survive incorporation into the ligand at an earlier step.

In all of the above reactions described for preparing compounds of this invention, groups such as sulfur groups, amine groups and ketone groups may be protected where appropriate during the various reactions, and the so-protected resulting products thereafter deprotected by known techniques.

Preferred Compounds

Compounds of the formula I are preferred where n, n1 and m2 are 0 and therefore Q is $(C(RR))_{m1}$; R and R* are independently H or alkyl groups, especially unsubstituted lower alkyl groups such as methyl; and at least one $R^2$ is hydrogen.

Particularly preferred compounds are those where Q is $(CH_2)_2$ or $(CH_2)_3$; the remaining R and R* groups are $CH_3$; $G^1$ is OH or $NH_2$; and $G^2$ is $NH_2$, $NHCH_3$, $NHC_6H_5$ or $NHC(O)C_6H_5$.

Preferred linking groups, and preferred $R^a$ groups, are discussed below.

Metal Complexes

The compounds of the formula I may be employed as ligands for the formation of metal complexes.

The metal complexes of the present invention 15 may be formed by complexing a compound of the formula I with a radioactive or non-radioactive metal, including a metal having an atomic number 22–31, 39–49 or 73–82, especially rhenium or technetium, preferably under basic conditions.

An exemplary method for the formation of a metal complex of the present invention is that where a complex or salt of the desired metal in the desired oxidation state and containing one or more easily displaceable (i.e., labile) ligands (for example, $H_2O$, halogen (eg., Cl), $NO_3^-$, or sugars) is mixed with ligand(s) of the present invention at a pH value suitable for forming the desired complex. Tke labile ligand is displaced from the metal by the ligand(s) of the present invention to form a metal complex of the present invention.

Illustrations of these methods are shown below:

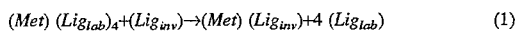

(1)

where

Met is a metal in a desired oxidation state;

$Lig_{lab}$ is a labile ligand such as $H_2O$, $Cl^-$, $Br^-$, $F^-$ or $NO_3^-$; and $Lig_{inv}$ is a ligand of the present invention.

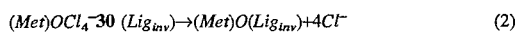

(2)

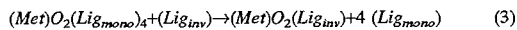

(3)

where Ligmono is a monodentate ligand such as pyridine, halogen, phosphine or amine.

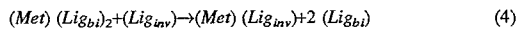

(4)

or

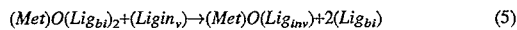

(5)

where $Lig_{bi}$ is a bidentate ligand such as a sugar, a diol, a bisamine, bipyridine or phosphine, and where, for each equation (1) to (5) above, the appropriate charge balance is employed.

Alternatively, the metal complexes of the present invention may be prepared from a metal in an oxidation state different from that of the desired complex. An example of such a method is that where either a reducing agent or an oxidizing agent (depending on the oxidation state of the metal used, and the oxidation state of the desired final product) is added to the reaction mixture containing metal to bring the metal to the desired oxidation state. The oxidant or reductant may optionally be used to form an intermediate complex in the desired oxidation state but with labile ligands which are then displaced by a desired chelating ligand of the present invention; or the oxidant or reductant may be added to the reaction mixture containing metal along with the desired ligand to achieve the change to the desired oxidation state and chelation to the desired metal in a single step.

Exemplary metal complexes of the present invention may be shown as the following formula I complex:

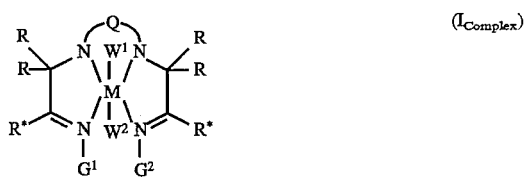

(I_Complex)

where the R and R* groups are as defined above, and where M can be a radioactive or non-radioactive metal which may optionally have other ligand(s) $W^1$ and/or $W^2$ in the unfilled coordination sites thereof. A hydrogen bond may be formed between $G^1$ and $G^2$ on complex formation. This will enhance the stability of the complex relative to a non-hydrogen bonded complex. Radioactive metals, for example, technetium, are preferred in these complexes. Preferably, in the cases where M is rhenium or technetium, the

portion can be shown as

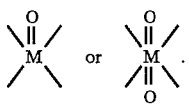

Other suitable co-ligands, $W^1$ and $W^2$, to form these complexes may include, but are not limited to, mono-, di- or tridentate ligands which, when combined with the ligands I form neutral metal complexes, particularly of technetium or rhenium, with the metal preferably in the +5 oxidation state.

The metal complexes of the present invention find utility as diagnostic and/or therapeutic agents. Thus, the present invention provides methods for the diagnosis of the presence and/or status of a disease state, or for the treatment of a disease state, comprising the step of administering a metal complex of the present invention to a subject in need thereof. The metal complexes of the present invention may be administered by any appropriate route such as orally, parenterally (for example, intravenously, intraperitoneally, intramuscularly or subcutaneously), or by any other suitable method. For example, the complexes of this invention may be administered to a subject by bolus or slow infusion intravenous injection.

The amount administered may be selected based on the desired use, such as to produce a diagnostic image of an organ or other site of a subject or a desired radiotherapeutic effect, by methods known in the art. Exemplary dosages are those employing about 30–200 mCi rhenium (for radiotherapy) or about 10–60 mCi technetium (for imaging). The "subject" of the methods of the present invention is preferably a mammal such as a domestic mammal, for example, a dog, cat, horse or the like, or most preferably, a human. Depending upon the metal and ligand used, the complexes of the present invention may be employed as, for example, imaging agents useful for imaging organs such as the heart or brain (where the complex may cross the blood-brain barrier), or for imaging the hepatobiliary system. The complexes of the invention are especially useful when attached to a biolocalizing moiety, for example, for the imaging of hypoxic tissue, and as therapeutic agents, such as hypoxic tissue cytotoxins, or radiosensitizers.

Metal complexes which have a permeability through cell membranes greater than that of $^{14}C$-sucrose, such as those containing a hypoxia-localizing moiety, are one embodiment of the diagnostic or therapeutic methods of the present invention. Cell permeability is a property of a cell membrane which describes the mobility of extraneous molecules (permeants) within the internal structure of the membrane (Stein, "Transport and Diffusion Across Cell Membrane", *New York Academic Press Inc.* (1986); Kotyk et al., *Biophysical Chemistry of Membrane Functions*, Chichester, UK: John Wiley & Sons (1988)). Molecules to which the membrane is permeable are able to penetrate through the membrane to reach the environment on the opposite side. Cell permeability may be determined by methods such as those described in U.S. patent application Ser. No. 08/054,120, filed Apr. 27, 1993, now abandoned, by Linder et al. (Attorney Docket No. RB90b), incorporated herein by reference.

Preferred complexes of the present invention are those comprising a compound of the formula I complexed with a radionuclide such as technetium or rhenium.

Rhenium is useful as a radiotherapy agent. The rhenium employed is generally one of the radionuclides Re-186 or Re-188, or a mixture thereof, which mixture may also include Re-185 and/or Re-187. Preparation of the complexes of the present invention where the metal is rhenium may be accomplished using rhenium in the +5 or +7 oxidation state. Examples of compounds in which rhenium is in the Re(VII) state are NH4ReO4 or KReO4. Re(V) is available as, for example, [ReOCl4](NBu4), [ReOCl4](Asph4), ReOCl3 (PPh3)2 and as ReO2(pyridine)4+. (Ph is phenyl; Bu is n-butyl). Other rhenium reagents, such as "carrier rhenium", capable of forming a rhenium complex may also be used. The phrase "carrier rhenium" means that the rhexlium compounds used contain non-radioactive rhenium at concentrations >10⁻⁷M.

Technetium is particularly useful as a diagnostic imaging agent. The technetium employed is preferably one or more of the radionuclides $^{99m}Tc$, $^{94m}Tc$ or $^{96m}Tc$. The preferred radioisotope for medical imaging is $^{99m}Tc$. Its 140 keV γ-photon is ideal for use with widely-available gamma cameras. It has a short (6 hour) half life, which is desirable when considering patient dosimetry. $^{99m}Tc$ is readily available at relatively low cost through commercially-produced $^{99}Mo/^{99m}Tc$ generator systems. Preparation of the complexes of this invention where the metal is technetium may be accomplished using technetium in the form of the pertechnetate ion. For $^{99m}Tc$, the pertechnetate ion is preferably obtained from commercially available technetium-99m parent-daughter generators; such technetium is in the +7 oxidation state. The generation of the pertechnetate ion using this type of generator is well known in the art, and is described in more detail in U.S. Pat. Nos. 3,369,121 and 3,920,995. These generators may generally be eluted with saline solution, and the pertechnetate ion obtained as the sodium salt. Pertechnetate may also be prepared from cyclotron-produced radioactive technetium using procedures well known in the art.

The formation of a technetium complex is preferably achieved by mixing pertechnetate ion in normal saline with the appropriate ligand. An appropriate buffer or physiologically acceptable acid or base may be used to adjust the pH to a value suitable for labeling the ligand. This appropriate value of pH will vary depending upon the nature of the ligand; for example, for ligands of the formula I, a pH in the range between ~5.5 to ~9.5 is suitable, preferably a pH value in the range of 7.0 to 8.5. A source of reducing agent may then be added to bring the pertechnetate down to the oxidation state of Tc(V) for chelation with the ligand. Stannous ion is the preferred reducing agent, and may be introduced in the form of a stannous salt such as stannous chloride, stannous fluoride, stannous tartrate, stannous diethylenetriamine pentaacetic acid or stannous citrate, or the like. The reaction is preferably run in an aqueous or aqueous/alcohol mixture, at or about room temperature, using a reaction time of about 1 minute to about 1 hour. The reducing agent is preferably present at a concentration of 5 to 50 µg/mL. The ligand is preferably present in a concentration of 0.5 to 2 mg/mL. Optionally, co-ligands $W^1$ and $W^2$ discussed above may be added.

Alternatively, the technetium complexes of this invention may be prepared by ligand exchange. A labile Tc(V) complex may be prepared by the reduction of $TcO_4^-$ in the presence of a ligand which forms a labile technetium complex, such as ethylene glycol, mannitol, or the hydroxycarboxylate ligands glucoheptonate, gluconate, citrate, malate or tartrate, at a pH value which is appropriate for the exchange ligand employed (usually 5 to 8). A reducing agent, such as the stannous salts described above, may be added, causing the formation of a labile reduced complex of Tc with the exchange ligand. This reduced Tc complex is then mixed with the ligand ultimately desired, at an appropriate pH value (as described above). The labile exchange ligand is displaced from the metal by the desired ligand, thus forming the technetium complexes of this invention.

Metal complexes of the present invention are preferred in which a compound described above under the section entitled "Preferred Compounds" is complexed with a metal, most preferably, with rhenium or technetium. Ligands which form single, neutral complexes are preferred. Exemplary complexes include those having the following structures:

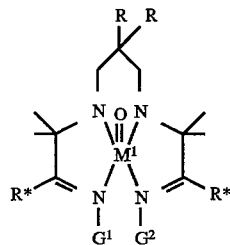

where $M^1$ is technetium.

While metal complexes of the present invention containing one or more bioactive groups as described below are useful, those complexes of the present invention lacking such groups are also useful, for example, in flow or organ imaging. Preferred complexes lacking bioactive group (s) are those produced from lipophilic ligands suitable for imaging the heart, brain or hepatobiliary system, or anionic or cationic groups suitable for imaging renal or hepatic function.

Bioactive Groups

A bioactive group ($R^a$) of the compounds of the present invention is capable of functioning as a metabolic substrate, catalyst or inhibitor, for example, to aid in clearance of the complex from non-target tissue; or is capable of being preferentially taken up at a selected site of a subject, such as by possessing an affinity for a cellular recognition site such as a receptor, enzyme or transport mechanism; or contain reactive groups for coupling to proteins; or effects tissue localization by another biochemical process. Thus, complexes of the present invention are contemplated where one or more bioactive groups are bound to the remainder of the complex which retain their desired bioactivity when so bound.

Exemplary bioactive groups include amphetamines, barbiturates, sulfonamides, monoamine oxidase substrates and inhibitors, hormones, enzymes, lipids, ligands for cell membrane receptors, antihypertensives, neurotransmitters, amino acids and oligopeptides, radiosensitizers, steroids (such as estrogen or estradiol), monoclonal or polyclonal antibodies or fragments thereof, carbohydrates (such as glucose derivatives), fatty acids, substrates for muscarinic receptors (such as 3-quinuclidinyl benzilate), substrates for dopamine receptors (such as spiperone), biotin, peptides and proteins which bind to specific receptors, substrates for benzodiazepine receptors and hypoxia-localizing moieties.

Complexes of the present invention containing bioactive groups are useful in that they employ properties, e.g., receptor binding, metabolism, etc., of a particular biochemically active group to provide imaging or treatment of a particular site or function. These complexes, especially where the metal is $^{99m}Tc$, provide highly effective, relatively easy to use diagnostic imaging products which are characterized by a covalent bond between the radionuclide complex and the bioactive group while substantially retaining the uptake properties of the free bioactive group. Examples of diagnostic uses for the complexes of the present invention include, but are not limited to, imaging of hypoxic tissue, e.g., in the heart, brain, lungs or in tumors; imaging of the brain and lungs when the bioactive group is a lipophilic amine-containing compound, e.g., an amphetamine; imaging of the brain, heart or tumors when the bioactive group is a sugar (e.g., a glucose derivative); imaging of the heart when the bioactive group is a fatty acid; imaging of steroid receptor sites when the bioactive group is a steroid (e.g., an estrogen for imaging breast carcinoma); and imaging of sites of infection when the bioactive group is a chemotactic peptide with affinity for blood cell types which localize at the site of infection.

In addition to diagnostic agents, the present invention also provides stably bound complexes for radiotherapeutic indications such as those indications described in U.S. Pat. No. 4,871,836. For example, Re complexes of the present invention which include estradiols can be used in the treatment of breast carcinoma. Also, to the extent that hypoxic tissue is known to be present in tumors, Re complexes of the present invention where the bioactive group is a hypoxia-localizing moiety are suitable for radiotherapy. The complexes of this invention where the metal is Re, for use in radiotherapy, are preferably injected into humans and allowed to concentrate at the desired site. Targeting of the radionuclide to a desired site with great specificity may thus be achieved. Radiotherapy is contemplated for those areas where a sufficient quantity of interacting sites (for example, estrogen receptors or hypoxic tissue) are present so as to provide therapeutic levels of the radionuclide to the area needing treatment.

When the bioactive group $R^a$ is asteroid, it is understood that either asteroid, a substituted steroid derivative or a non-steroidal derivative may be employed provided that the $R^a$ group chosen has an affinity for the steroid receptor. For example, $R^a$ may be the steroid estradiol:

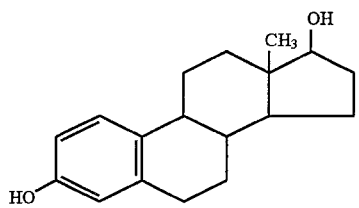

The estradiol group may be bonded to the remainder of the complex at any available position on the molecule, but is preferably bonded through a linking group to either an atom in the B ring or an atom in the D ring. Additionally, the estradiol molecule may be substituted at available positions by one or more R groups where R is as defined above. Alternatively, the steroid molecule may be replaced by a non-steroidal diol with a known affinity for the estrogen receptor, such as

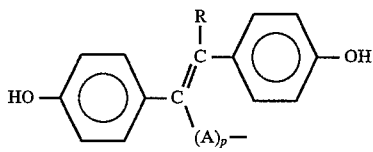

where $(A)_p$ and R are as defined above.

When the bioactive group is a substrate for a muscarinic receptor, the $-(A)_p-R^a$ portion of the complex is preferably the group:

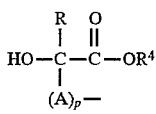

where $(A)_p$ and R are as defined above and $R^4$ is a tertiary or quaternary amine, such as 3-quinuclidinol or a substituted 3-quinuclidinol, or the following compounds:

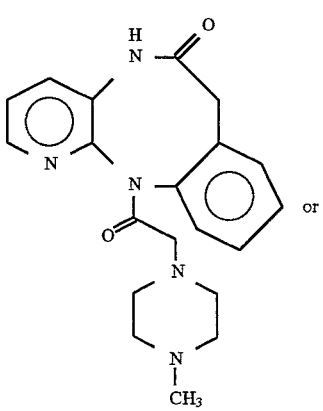

pirenzepin

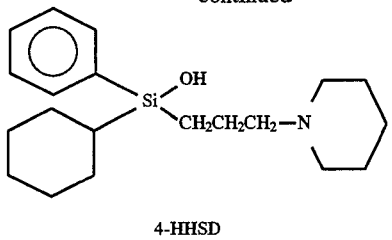

4-HHSD

Linking Groups

The linking group(s) (A)p of the compounds of the present invention, when present (that is, when p is greater than zero), may be any one or more moieties which can serve to distance physically, or otherwise isolate, the bioactive group from the remainder of the compound of the formula I or complex thereof. The presence of such linking group(s) may be desirable, for example, where a bioactive group may be inhibited in its action by the remainder of the complex. In considering the various linking groups which may be employed, it is understood that p may be any convenient value depending upon the design choice for the desired complex. Preferably, p is $\leq 20$ and is most preferably $\leq 10$.

Examples of linking groups which may be employed alone (where p is one), or together to form a straight or branched chain (where p is greater than one) and which may be bonded to the remainder of the ligand from either end are: —$CH_2$—, —$CHR^5$, —$CR^5R^6$—, —CH=CH—, —CH=$CR^5$—, —$CR^5$=$CR^6$—, —C≡C—, cycloalkyl, cycloalkenyl, aryl (e.g., p-phenylene or hydroxy substituted p-phenylene), heterocyclo, oxygen, sulfur, —C(O)—, —NH—, —HC=N—, —$CR^5$=N—, —$NR^5$— and —CS—; wherein $R^5$ and $R^6$ are independently selected from alkyl, alkenyl, alkoxy, aryl, 5- or 6-membered nitrogen- or oxygen-containing heterocycles, halogen, hydroxy or hydroxyalkyl.

When present, the preferred values for (A)p (bonded to the remainder of the ligand from either end) are alkyl, oxa-alkyl, hydroxyalkyl, hydroxyalkoxy, alkenyl, arylalkyl, arylalkylamide, alkylamide, alkylamine and (alkylamine) alkyl.

The most preferred values for (A)p are selected from the following (bonded to the remainder of the ligand from either end): —($CH_2$)1—5— (especially methyl or ethyl), —$CH_2$—CH=CH—$CH_2$—, —($CH_2$)1—2—C(O)—NH—($CH_2$)1—3—, —$C_6H_5$—($CH_2$)1—2—, —($CH_2$)1—2—CH(OH)—$CH_2$—, —($CH_2$)$_2$O—, —$CH_2$CH(OH)$CH_2$O$CH_2$—, —$CH_2$—C(O)—NH—CH—$C_6H_5$—, —(A'—O—A")1—3, and —(A'—NH—A")1—3; where A' and A" are the same or different alkyl or aryl groups and $C_6H_5$ is p-phenylene.

Kits for Forming Metal Complexes

It is convenient to prepare the complexes of the present invention at, or near, the site where they are to be used. A single, or multi-vial kit that contains all of the components needed to prepare the complexes of this invention, other than the radionuclide ion itself, is an integral part of this invention.

A preferred single-vial kit of the present invention comprises a ligand of the formula I and a source of a pharmaceutically acceptable reducing agent such as a stannous salt. Most preferably, in addition, the kit is buffered with a pharmaceutically acceptable acid or base to adjust the pH to a desired value for complex formation as described above. It is preferred that the kit contents be in lyophilized form.

Such a single vial kit may optionally contain exchange liganas such as glucoheptonate, gluconate, mannitol, malate, citric or tartaric acid and may also contain reaction modifiers, such as diethylenetriaminepentaacetic acid or ethylenediamine tetraacetic acid. Additional additives, such as solubilizers (for example α-, β- or γ-cyclodextrin), anti-oxidants (for example ascorbic acid), fillers (for example, sodium chloride) may be employed to improve the radiochemical purity and stability oE the final product, or to aid in the production of the kit.

A preferred multi-vial kit of the present invention comprises, in one vial, the components, other than the radionuclide itself, required to form a labile radionuclide (especially Tc(V)) complex as described above, that is, an exchange ligand and a pharmaceutically acceptable reducing agent such as a stannous salt. The quantity and type of exchange ligand, and amount and type of reducing agent and buffer used may be selected based on the nature of the exchange complex to be formed. The ligand I of the present invention is contained in a second vial, as well as optional additives such as buffers appropriate to adjust the pH to its optimal value.

A single vial kit may be ready for use following addition of the radionuclide ion, such as pertechnetate. A multi-vial kit may be ready for use by addition of the radionuclide ion, such as pertechnetate, to the vial containing exchange ligand and reducing agent, and after waiting an appropriate period of time for formation of a labile complex, the contents of this vial are added to the second vial containing a source of the desired ligand. After a reaction time of about 1 to 60 minutes, the complex of the present invention is formed. It is advantageous that the contents of both vials of this multi-vial kit be lyophilized. As described for the single vial kit, additional additives may be employed to improve the radiochemical purity and stability of the final product, or to aid in the production of the kit.

Alternatively, the multi-vial kit may comprise the desired ligand in one vial and a source of reducing agent such as stannous ion in a second vial. Pertechnetate may be added to the vial containing ligand, and then the contents of the second vial added to initiate labeling. As above, the quantity and type of ligand, buffer pH and reducing agent may be selected based on the nature of the desired ligand used. Again, it is advantageous that the contents of both vials be lyophilized.

All stereoisomers of the compounds and complexes of the present invention are contemplated herein, whether alone (that is, substantially free of other isomers), in a mixture of certain stereoisomers (for example, as a racemate) or in any other mixture thereof.

The following Examples further illustrate specific embodiments of this invention, and should not be construed to limit the scope or spirit of the present claims.

EXAMPLE 1

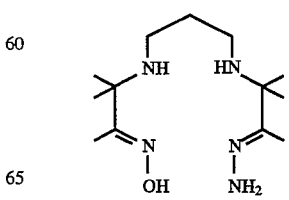

Synthesis of 3,3,9,9-tetramethyl-4,8-diazaundecane-2,10-dione 2-hydrazone 10-oxime A. 3-Chloro-3-methyl-2-nitrosobutane A solution of 2-methylbut-2-ene (37 mL, 0.35 mol) and isoamyl nitrite (39.0 mL, 0.29 mol) was cooled to −10° C. in a carbon tetrachloride-dry ice bath. Concentrated hydrochloric acid (35 mL) was added dropwise at −5° C. over 1 hour. The green solution was stirred for an additional 30 minutes. The precipitated solid was isolated by filtration, washed with cold ethanol (−20° C., 3×10 mL), and partially dried under a stream of nitrogen. After drying in vacuo for 2 hours, 21.8 g of white solid was obtained (55%); mp. 72°–74° C. $^1$H NMR (CDCl$_3$) δ 5.97 (1, 1H), 1.68 (s, 3H), 1.65 (s, 3H), 1.50 (d, 3H).

B. 3-Bromo-3-methyl-2-butanone

Bromine (450 g) in dry carbon tetrachloride (200 mL) was added dropwise over 3 hours to a solution of isopropyl methyl ketone (258 g) in dry carbon tetrachloride (500 mL). The temperature was maintained at 0° C. and moisture was excluded from the reaction vessel. After the addition, the reaction mixture was stirred at room temperature for 16 hours. Carbon tetrachloride and other volatiles were removed under aspirator vacuum at 50°–60° C., and the residual dark liquid was distilled off by raising the temperature to 100°–110° C. under aspirator vacuum. The yellow liquid thus obtained was distilled three times using a 6 inch fractionating column, and the fraction boiling at 139°–142° C. was collected. Yield: 206 g; bp. 139°–142° C. $^1$H NMR (CDCl$_3$) δ 2.45 (s, 3H) and 1.85 (s, 6H). (Lit. Pfleiderer, W.; Zondel, H. Leibigs Ann. Chem. 1966, 99, 3008).

C. N-(3-Aminopropyl)-1-amino-1,1-dimethyl-2-butanone oxime

A solution of Compound A (20.3 g, 0.15 mol) in methanol (250 mL) was added dropwise to a stirred solution of 1,3-diaminopropane (50 mL, 0.60 mol) in methanol (100 mL) at 0° C. After the addition was completed, the reaction mixture was refluxed for 6 hours. Methanol was removed on a rotary evaporator and water (100 mL) was added. The resultant white precipitate was removed by filtration. The filtrate was saturated with sodium chloride and extracted with dichloromethane (5×100 mL). The combined organic extracts were dried over anhydrous magnesium sulfate and then evaporated under reduced pressure to give a yellow oil. Crystallization with acetonitrile gave the product as a white crystalline solid (12.96 g, 50%); mp. 70°–72° C. MS (CI): MS m/e (M+H)$^+$=174. $^1$H NMR (CDCl$_3$) δ2.77 (t, 2H), 2.48 (t, 2H), 1.48 (s, 3H), 1.63 (m, 2H), 1.24 (s, 6H).

D. 4,8-Diaza-3,3,9,9-tetramethylundecane-2,10-dione monoxime

Compound C (0.53 g, 3.06 mmol) and Compound B (0.56 g, 3.39 mmol) were added to a suspension of anhydrous potassium carbonate (0.47 g, 3.62 mmol) in dry dimethylformamide (2 mL). The mixture was stirred at room temperature under nitrogen atmosphere for 18 hours. Ether (30 mL) was added and the mixture was filtered to remove the precipitated solid. The solvent was removed under vacuum and the resultant semi-solid was triturated with hexane to give the product as a colorless crystalline solid. Yield: 0.64 g (81%); mp. 71°–72° C.; TLC [silica gel, dichloromethane:methanol 9:1] R$_f$ 0.30. $^1$H NMR (CDCl$_3$) δ 1.24 (2S, 12H, gem-CH$_3$), 1.65 (m, 4H, NHCH$_2$CH$_2$), 1.86 (s, 3H, N(OH)CCH$_3$), 2.18 (s, 3H, COCH$_3$) and 2.45 (t, 4H, NHCH$_2$); MS m/e (M+H)$^+$=258.

E. 3,3,9,9-tetramethyl-4,8-diazaundecane-2,10-dione 2-hydrazone 10-oxime

A solution of Compound D (0.6 g, 2.34 mmol) and hydrazine hydrate (0.31 g, 4.70 mmol) in ethanol (3 mL) was stirred at room temperature for 18 hours. The reaction mixture, after evaporation of the solvent, afforded the product as a colorless crystalline solid. Yield: 0.6 g (95%); mp. 125°–126° C.; TLC [silica gel, dichloromethane:methanol 8:2] R$_f$ 0.21. $^1$H NMR (CDCl$_3$) δ 1.22 (2s, 12H, gem-CH$_3$), 1.58 (m, 4H, NHCH$_2$, CH$_2$), 1.76 (s, 3H, N(NH$_2$)CCH$_3$), 1.86 (s, 3H, N(OH)CCH$_3$), 2.41 (m, 4H, NHCH$_2$) and 5.01 (s, 2H, NNH$_2$); MS: (M+H)$^+$=272; HRMS Eor C$_{13}$H$_{30}$N$_5$O (M+H)$^+$ calc'd 272.2540; found 272.2457. Anal. Calc'd for C$_{13}$H$_{29}$N$_5$O·0.14 H$_2$O. 0.14 Hexane: C, 58.12; H, 11.01; N, 24.49. Found: C, 58.14; H, 11.18; N, 24.39.

EXAMPLE 2

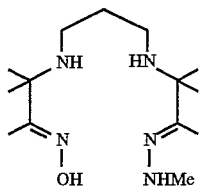

Synthesis of 3,3,9,9-tetramethyl-4,8-diazaundecane-2,10-dione 2-(2-methylhydrazone) 10-oxime A solution of Compound D from Example 1 (0.5 g, 1.95 mmol) in methanol (3 mL) was treated with methylhydrazine (0.17 g, 3.70 mmol) and stirred for 15 hours. The paste which resulted from evaporation of the volatiles under vacuum was dissolved in methanol saturated with HCl (5 mL). The solvent was removed, and the resultant solid was recrystallized from methanol-ether to give the product trihydrochloride salt as a colorless crystalline solid in 75% yield (0.42 g); mp 175°–177° C. $^1$H NMR (D$_2$O) δ 1.46 (s, 6H, C(CH$_3$)$_2$); 1.55 (s, 6H, C(CH$_3$)$_2$); 1.85 (s, 3H, CCH$_3$); 2.06 (m, 2H, CH$_2$CH$_2$CH$_2$); 2.14 (s, 3H, CCH$_3$); 3.01 (s, 3H, NHCH$_3$); 3.15 (m, 4H, NHCH$_2$). MS: (M+H)$^+$=286. HRMS for C$_{14}$H$_{32}$N$_5$O (M+H)$^+$ Calc'd 286.2607; Found 286.2595. Anal. Calc'd for C$_{14}$H$_{31}$N$_6$O·3HCl·0.60 H$_2$O: C, 41.46; H, 8.75; N, 17.27; Cl, 26.22. Found: C, 41.66; H, 9.13; N, 17.11; Cl, 26.18.

EXAMPLE 3

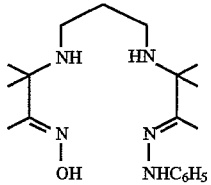

Synthesis of 3,3,9,9-tetramethyl-4,8-diazaundecane-2,10-dione 2-(2-phenyl-hydrazone) 10-oxime A solution of phenylhydrazine hydrochloride (0.425 g, 2.94 mmol) and sodium hydroxide (0.12 g, 3.0 mmol) in dry methanol (5.0 mL) was stirred at 0° C. for 1 hour and filtered to remove the sodium chloride which formed. This solution was added to Compound D from Example 1 (0.5 g, 1.95 mmol) in methanol (1 mL) and the mixture was stirred at room temperature for 15 hours. After evaporation of the solvent under vacuum, the resultant paste was triturated with hexane, and the solid which formed was isolated and recrystallized from ether to afford the product as a colorless solid in 60% yield (0.40 g); mp 145°–146° C. $^1$H NMR (CDCl$_3$) δ 1.22(s, 6H, C(CH$_3$)$_2$); 130(s, 6H, C(CH$_3$)$_2$); 1.60(m, 2H, CH$_2$CH$_2$CH$_2$); 1.89(s, 3H, CCH$_3$); 2.45(m, 4H, NHCH$_2$); 6.96(s, 2H, N=NH); 6.82, 7.08 and 7.23 (m, 5H, C$_6$H$_5$).

MS:(M+H)⁺=348. HRMS for $C_{19}H_{34}N_5O$ (M+H)⁺ Calc'd 348.2763, Found 348.2765. Anal. Calc'd for $C_{19}H_{33}N_5O$: C, 65.67; H, 9.57; N, 20.15. Found: C, 65.81; H, 9.88; N, 20.19.

EXAMPLE 4

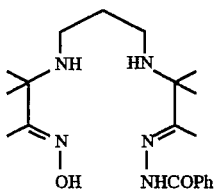

Synthesis of 3,3,9,9-tetramethyl-4,8-diazaundecane-2,10-dione 2-(2-benzoylhydrazone) 10-oxime Benzoic hydrazide (0.29 g, 2.13 mmol) was added to a solution of Compound D from Example 1 (0.5 g, 1.95 mmol) in methanol (3.0 mL), and the reaction mixture was stirred at room temperature for 48 hours. The solvent was removed under vacuum to afford a cream colored paste which on trituration with ether provided the product as a crystalline solid. For further purification, the compound was loaded onto a reversed phase $C_{18}$ column (4.60×25 cm) and eluted with 4% acetonitrile/H20 (0.1% TFA). The fractions with compound (analyzed by analytical HPLC) were collected and freeze-dried to afford a colorless solid of the title compound. Yield: 0.41 g (53%); mp. 95°–96° C. (bis-trifluoroacetate salt). ¹H NMR (D₂O) δ 1.42 & 1.55(2s, 6H, C(CH₃)₂), 1.80 & 2.05(2s, 6H, CCH₃), 2.12(m, 2H, CH₂CH₂CH₂), 3.18(m, 4H, NHCH₂) and 7.42, 7.55 & 7.72(m, 5H, C₆H₅). MS:(M+H)⁺=376. HRMS for $C_{20}H_{34}N_5O_2$ (M+H)⁺ Calc'd 376.2713, Found 376.2714. Anal. Calc'd for $C_{20}H_{33}N_5O_2 \cdot 2CF_3COOH \cdot 1.26H_2O$: C, 46.03; H, 6.04; N, 11.18. Found: C, 46.12; H, 5.79; N, 11.09.

EXAMPLE 5

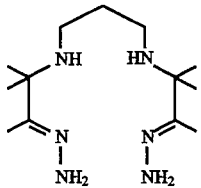

Synthesis of 3,3,9,9-tetramethyl-4,8-diazaundecane-2,10-dione bishydrazone

A. 4,8-Diaza-3,3,9,9-tetramethylundecane-2,10-dione 1,3-Diaminopropane (0.3 g, 4.0 mmol) and Compound B from Example 1 (1.65 g, 10.0 mmol) were added to a suspension of anhydrous potassium carbonate (1.38 g, 10.00 mmol) in dry tetrahydrofuran (10 mL), and the mixture was stirred at room temperature under nitrogen atmosphere for 18 hours. Dichloromethane was added and the mixture was stirred for 10 minutes and filtered. The filtrate was evaporated under vacuum to provide a light yellow oil which was purified on a silica gel column with 2% methanol in dichloromethane as eluant. The fractions with product were combined and the solvent evaporated to give Compound A as a colorless oil in 94% yield (0.92 g). ¹H NMR (CDCl₃) δ 1.88[s, 6H, C(CH₃)₂], 1.55(m 2H, CH₂CH₂CH2), 1.85(bs, 2H, NH), 2.18(s, 6H, COCH₃) and 2.40(m, 4H, NHCH₂). MS:(M+H)⁺=243.

B. 3,3,9,9-tetramethyl-4,8-diazaundecane-2,10-dione bishydrazone

Hydrazine hydrate (0.4 g, 6.06 mmol) was added to a solution of Compound A (0.50 g, 2.07 mmol) in methanol (3 mL), and the mixture was stirred at room temperature for 18 hours. The solvent was removed on a rotary evaporator and the resultant paste was triturated with petroleum ether (35°–60° C.) to give a colorless solid. The solid was isolated and crystallized from ethyl acetate-hexane to afford the product in 80% yield (0.45 g); mp 95°–96° C. ¹H NMR (CDCl₃) δ 1.98(s, 12H, C(CH₃)2), 1.55(m, 4H, CH₂CH₂CH₂ and NHCH₂), 1.74(s, 6H, NCCH₃), 2.40(t, J=7.0 Hz, 4H, NHCH₂) and 4.95 (s, 4H, NNH₂); MS:(M+H)⁺=271. HRMS for $C_{13}H_{31}N_6$ (M+H)⁺ Calc'd 271.2610, Found 271.2599. Anal. Calc'd for $C_{13}H_{30}N_6 \cdot 0.44 H_2O$: C, 56.08; H, 12.39; N, 30.18. Found: C, 56.16; H, 12.43; N, 30.11.

EXAMPLE 6

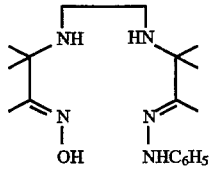

Synthesis of 3,3,6,8-tetramethyl-4,8-diazadecane-2,9-dione 2-(2-phenylhydrazone) 9-oxime A. N-(2-Aminoethyl)-3-amino-3-methyl-2-butanone oxime A solution of Compound A from Example 1 (10 g, 73.8 mmol) was added dropwise to a stirred solution of 1,2-diaminoethane (25 g, 416.7 mmol) in methanol (10 mL}at 0° C. After the addition was complete, the mixture was left overnight at room temperature with stirring. Removal of the methanol in vacuo gave a light yellow oil which was dissolved in water. The pH of the solution was adjusted to about 11. The solvent was removed under vacuum, and the residue was extracted with ethyl acetate. Evaporaticn of the organic phase gave a light yellow semi-solid which on crystallization with ether gave the product as a crystalline solid. Yield: 5.89 g (50%); mp. 65°–67° C. ¹H NMR {CDCl₃) δ 1.22[s, 6H, C(CH₃)₂], 1.87[s, 3H, C(=N)CH₃], 2.49(t, 2H, CH₂NH₂) and 2.88(m, 2H, NHCH₂). MS:(M+H)⁺=160.

B. 4,7-Diaza-3,3,8,8-tetramethyldecane-2,9-dione monoxime

Compound B from Example 1 (1.14 g, 6.91 mmol) and K₂CO₃ (0.95 g, 6.91 mmol) were added to a solution of N-(2-aminoethyl)-1-amino-1,1-dimethyl-2-butanone oxime (1.0 g, 6.29 mmol) in dry dimethylformamide (5 mL), and the reaction mixture was stirred at room temperature for 15 hours. Dichloromethane was added to the reaction mixture, which was then stirred for 10 minutes and filtered to remove the solid materials. Evaporation of the solvent under vacuum gave a yellow paste which on crystallization from ether-hexane afforded the product as a colorless solid. Yield: 1.15 g (75%); mp. 96°–97° C. ¹H NMR (CDCl₃) δ 1.25[2s, 12H, C(CH₃)₂], 1.87[s, 3H, C(=NOH)CH₃], 2.22[s, 3H, C(=O)CH₃] and 2.52(s, 4H, CH₂NH). MS:(M+H)⁺=244.

C. 4,7-Diaza-3,3,8,8-tetramethyldecane-2,9-20 dione-2-oxime 9-phenylhydrazone

A solution of Compound B (0.5 g, 2.06 mmol) in methanol (5 mL) was treated with phenyl-hydrazine.HCl (0.326 g, 2.26 mmol) and sodium acetate (0.30 g, 2.26 mmol). The reaction mixture was stirred at room temperature for 8 hours. After evaporation of the solvent, the resultant yellow paste was crystallized from dichloromethane-hexane to provide the product as a colorless crystalline solid; yield: 0.25 g (58%); mp. 95°–97° C. $^1$H NMR (CDCl$_3$) δ 1.98(s, 12H, C(CH$_3$)$_2$), 1.55(m, 4H, CH$_2$CH$_2$CH$_2$ and NHCH$_2$), 1.74(s, 6H, NCCH$_3$), 2.40(t, J=7.0 Hz, 4H, NHCH$_2$) and 4.95 (s, 4H, NNH$_2$); MS:(M+H)$^+$=334. Anal. Calc'd for C$_{18}$H$_{31}$N$_5$O·0.91H$_2$O: C, 61.79; H, 9.45; N, 20.02. Found: C, 61.84; H, 9.05; N, 19.97.

EXAMPLE 7

Preparation of the $^{99m}$Tc complexes of the liuand in Examples 1, 2 and 3

The ligands of Examples 1, 2 and 3 (about 1 mg) were each separately dissolved in saline (1 mL), 0.1 M sodium bicarbonate (0.5 mL) and technetium genarator eluate (0.5 mL). Saturated tin tartrate in saline (50 lμL) was added. After standing at room temperature for about 5 minutes, the radiochemical purity of each complex (as measured by HPLC; PRP-1 10 μm, acetonitrile/0.1M NH$_4$OAc pH 4.6 [either 70:30 or 40:60], 1 mL/min) was ≧90%.

EXAMPLE 8

Preparation of the $^{99m}$Tc complex of the ligand in Example 4

The ligand of Example 4 (4.4 mg) was dissolved in saline (1 mL), 0.1 M sodium bicarbonate (0.5 mL) and technetium generator eluate (0.5 mL). Saturated tin tartrate in saline (50 μL) was added. The reaction was complete in less than 5 minutes at room temperature. The radiochemical purity of the title complex was approximately 85%, as measured by HPLC analysis [Nucleosil C8, 60/40 ACN/0.02 M sodium phosphate (pH 7.4), 1 mL/min]. The radiochemical purity was improved by loading the reaction mixture onto a preconditioned C18 Sep-Pak (Sep-Pak™ plus), washing with 2 mL of 50% ethanol/saline and then eluting with 1 mL of ethanol. About 30% of the activity was recovered in the ethanol solution. The radiochemical purity of the purified compound in ethanol was 97.6%.

EXAMPLE 9

Preparation of the $^{99}$Tc complex of the ligand in Example 3

NaTc(O)(ethylene glycol)$_2$ (25.5 mg, 0.1 mmol) was dissolved in methanol (5 mL) and added to a solution of the ligand of Example 3 (34.7 mg, 0.1 mmol) in methanol (5 mL). The mixture was stirred for 15 minutes. Solvent was removed under reduced pressure. The orange oily residue was dissolved in dichloromethane, loaded onto a silica gel column and eluted with 5% methanol in dichloromethane. The orange product was recrystallized with dichloromethane/ether/hexane. Yield 11.2 mg (24%). Calc'd. for C$_{19}$H$_{30}$N$_5$O$_2$Tc·0.25 CH$_2$Cl$_2$:C, 48.10; H, 6.40; N, 14.57. Found: C, 48.30: H, 6.28; N, 14.25. NMR(CDCl$_3$): δ 7.26(t), 6.95(t), 6.85(d), 3.5 (m), 3.23(t), 2.40(S), 2.30(S), 1.66(S), 1.45(S), 1.43(S), 1.42(S). MS (FAB +): m/z=460 (M+H), 459 (M), 444 (M+H–O). IR (KBr): ν(cm$^{-1}$): 926 (Tc=O).

EXAMPLE 10

Preparation of the $^{99}$Tc complex of the ligand in Example 1

This compound was prepared by the same procedure as described above for Example 9 (yield 11%). NMR(CDCl$_3$): ε 3.5 (m), 3.21(t), 2.28(S), 2.22(S), 1.46(S), 1.45(S), 1.43 (S), 1.34(S). MS (FAB+): m/z=384 (M+H), 383 (M). IR (KBr) ν(cm$^{-1}$): 920 (Tc=O).

EXAMPLE 11

Preparation of the $^{99}$Tc complex of the ligand in Example 4

Ethylene glycol (30 μL, 0.55 mmol) was added to a stirring solution of methanol (1 mL) and tetrabutyl ammonium $^{99}$Tc(O)Cl$_4$ (32.3 mg, 0.065 mmol). A methanolic solution of sodium acetate (0.75 M, 0.3 mL) was then added dropwise, and the reaction was stirred for 15 minutes. The solution turned to deep purple indicating the formation of tetrabutyl ammonium [Tc(O)(Eg)$_2$]. The ligand of Example 4 (40.6 mg, 0.065 mmol) in methanol (1 mL) was added. The reaction mixture was stirred at room temperature for 15 minutes. Solvents were evaporated under reduced pressure. The brown residue was dissolved in 5 mL dichloromethane0 washed with 2×5 mL water, and dried with anhydrous sodium bisulfate. The dichloromethane solution was concentrated to approximately 1 mL, loaded onto a dichloromethane treated silica gel column (¾"×4"), and eluted with 2% methanol in dichloromethane. The orange band was collected. The product was recrystallized with dichloromethane/ether at –15° C. The orange crystals were collected by filtration, washed with 3×1 mL ether, and dried under vacuum. The yield was 5.2 mg (16%). MS [m/z (species)]: (FAB+): 488 (M+H), 470 (M—OH); (FAB—): 486 (M—H). $^1$H NMR (CDCl$_3$): δ 8.10 (m, 2H, phenyl), 7.48 (m, 3H, phenyl), 3.49 (m, 2H, CH$_2$), 3.41 (t, 2H, CH$_2$), 3.28 (t, 2H, CH$_2$), 2.39 (s, 3H, CH$_3$), 2.28 (s, 3H, CH$_3$), 1.67 (s, 3H, CH$_3$), 1.51 (s, 3H, CH$_3$), 1.45 (s, 3H, CH$_3$), 1.44 (s, 3H, CH$_3$). IR (KBr) ν (cm$^{-1}$):920 (Tc=O)

What we claim is:

1. A diagnostic method comprising: (a) administering an imaging effective amount to a mammalian subject in need thereof a complex comprising a radioactive metal complexed with a compound of the following formula I:

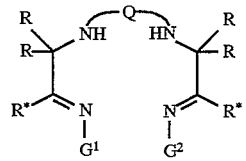

where Q is the group —(C(RR))$_{m1}$—(Y$^1$)$_n$—(C(RR))$_{m2}$—(Y$^2$—(C(RR))$_{m3}$)$_{n1}$—, where Y$^1$ and Y$^2$ are each independently —NR—, —O—, —S—, —SO—, —SO$_2$— or —Se—; n and n1 are each independently 0 or 1; and m1, m2 and m3 am each independently 0 or an integer from 1 to 4; provided that m1 and m2 are not both 0, that m1+m2+n+n1 is less than 6 and that a carbon atom bearing an R group is not directly bonded to more than one heteroatom; each R and R* group is independently:

(i) R$^1$;

(ii) alkoxy;

(iii) hydroxy;

(iv) halogen;

(v) haloalkyl;

(vi) —OR$^1$;

(vii) —C(O)—OR$^1$;

(viii) —C(O)—N(R$^1$)$_2$;

(ix) —N(R$^1$)$_2$—;

(x) —N(R$^1$)—COR$^1$;
(xi) —alkyl—C(O)—OR$^1$;
(xii) —alkyl—C(O)—N(R$^1$)$_2$;
(xiii) —alkyl—N(R$^1$);
(xiv) —alkyl—N(R$^1$)—COR$^1$;
(xv) —aryl—C(O)—OR$^1$;
(xvi) —aryl—C(O)l—N(R$^1$)$_2$;
(xvii) —aryl—N(R$^1$)$_2$;
(xviii) —aryl—N(R$^1$)—COR$^1$;
(xix) nitrile;
(xx) acyl;
(xxi) acyloxy;
(xxii) heterocyclo;
(xxiii) hydroxyalkyl;
(xxiv) alkoxyalkyl;
(xxv) hydroxyaryl;
(xxvi) arylalkyl;
(xxvii) —SO$_2$—R$^1$;
(xxviii) —alkyl—SO$_2$—R$^1$;
(xxix) —(A)$_p$—R$^a$, where A is a linking group which is bound to R$^a$ via a carbon, oxygen, nitrogen or sulfur group, p is 0 or a positive integer, and R$^a$ is a bioactive moiety or a reactive group which forms a covalent bond to a bioactive moiety; or
(xxx) two of the groups, taken together with one or more atoms to which they are bonded, form a saturated or unsaturated, spiro or fused, carbocyclic or heterocyclic ring which may be unsubstituted or substituted by one or more groups selected from the groups (i) to (xxix) above;

each R$^1$ is independently hydrogen, alkyl, alkenyl, alkynyl or aryl; and

G$^1$ and G$^2$ are each independently —OH or —N(R$^2$)$_2$, provided that at least one of G$^1$ and G$^2$ is —N(R$^2$)$_2$, where each R$^2$ is independently hydrogen, alkyl, aryl, acyl or —(A)$_p$—R$^a$;

each alkyl is substituted or unsubstituted and has 1 to 12 carbon atoms;

each alkoxy is substituted or unsubstituted and has 1 to 12 carbon atoms;

each alkenyl is substituted or unsubstituted and has 2 to 10 carbon atoms;

each alkynyl is substituted or unsubstituted and has 2 to 10 carbon atoms;

each cycloalkyl is substituted or unsubstituted and is a 1- to 3-ring system where each ring contains 3 to 7 carbon atoms;

each aryl is substituted or unsubstituted and is a homocyclic aromatic group which contains 1 or 2 rings where each ring contains 6 to 12 carbon atoms;

each heterocyclo is substituted or unsubstituted and is a saturated or unsaturated, aromatic or non-aromatic cyclic group containing at least one oxygen, nitrogen or sulfur atom;

each bioactive moiety is a group selected from the list consisting of a group which can function as a metabolic substrate, catalyst or inhibitor; a group which can preferentially be taken up at a selected biological site; a group which contains reactive groups for coupling to a protein; or a group which can preferentially localize at a selected biological site; and (b) imaging said subject.

2. The method of claim 1 where the metal of said complex is technetium.

3. A method of treatment of a disease comprising administering to a mammalian subject in need thereof a complex of a radioactive metal and a compound of the following formula:

where Q is the group —(C(RR))$_{m1}$—(Y$^1$)$_n$—(C(RR))$_{m2}$—(Y$^2$—(C(RR))$_{m3}$)$_{n1}$—, where Y$^1$ and Y$^2$ are each independently —NR—, —O—, —S—, —SO—, —SO$_2$— or —Se—; n and n1 are each independently 0 or 1; and m 1, m2 and m3 are each independently 0 or an integer from 1 to 4; provided that m1 and m2 are not both 0, that m1+m2+n+n1 is less than 6 and that a carbon atom bearing an R group is not directly bonded to more than one heteroatom; each R and R* group is independently:

(i) R$^1$;
(ii) alkoxy;
(iii) hydroxy;
(iv) halogen;
(v) haloalkyl;
(vi) —OR$^1$;
(vii) —C(O)—OR$^1$;
(viii) —C(O)—N(R$^1$)$_2$;
(ix) —N(R$^1$)$_2$—;
(x) —N(R$^1$)—COR$^1$;
(xi) —alkyl—C(O)—OR$^1$;
(xii) —alkyl—C(O)—N(R$^1$)$_2$;
(xiii) —alkyl—N(R$^1$);
(xiv) —alkyl—N(R$^1$)—COR$^1$;
(xv) —aryl—C(O)—OR$^1$;
(xvi) —aryl—C(O)—N(R$^1$)$_2$;
(xvii) —aryl—N(R$^1$)$_2$;
(xviii) —aryl—N(R$^1$)—COR$^1$;
(xix) nitrile;
(xx) acyl;
(xxi) acyloxy;
(xxii) heterocyclo;
(xxiii) hydroxyalkyl;
(xxiv) alkoxyalkyl;
(xxv) hydroxyaryl;
(xxvi) arylalkyl;
(xxvii) —SO$_2$—R$^1$;
(xxviii) —alkyl—SO$_2$—R$^1$;
(xxix) —(A)$_p$—R$^a$, where A is a linking group which is bound to R$^a$ via a carbon, oxygen, nitrogen or sulfur group, p is 0 or a positive integer, and R$^a$ is a bioactive moiety or a reactive group which forms a covalent bond to a bioactive moiety; or
(xxx) two of the groups, taken together with one or more atoms to which they are bonded, form a saturated or unsaturated, spiro or fused, carbocyclic or heterocyclic ring which may be unsubstituted or substituted by one or more groups selected from the groups (i) to (xxix) above;

each $R^1$ is independently hydrogen, alkyl, alkenyl, alkynyl or aryl; and $G^1$ and $G^2$ are each independently —OH or —$N(R^2)_2$, provided that at least one of $G^1$ and $G^2$ is —$N(R_2)_2$, where each $R^2$ is independently hydrogen, alkyl, aryl, acyl or —$(A)_p$—$R^a$;

each alkyl is substituted or unsubstituted and has 1 to 12 carbon atoms;

each alkoxy is substituted or unsubstituted and has 1 to 12 carbon atoms;

each alkenyl is substituted or unsubstituted and has 2 to 10 carbon atoms;

each alkynyl is substituted or unsubstituted and has 2 to 10 carbon atoms;

each cycloalkyl is substituted or unsubstituted and is a 1- to 3-ring system where each ring contains 3 to 7 carbon atoms;

each aryl is substituted or unsubstituted and is a homocyclic aromatic group which contains 1 or 2 rings where each ring contains 6 to 12 carbon atoms;

each heterocyclo is substituted or unsubstituted and is a saturated or unsaturated, aromatic or non-aromatic cyclic group containing at least one oxygen, nitrogen or sulfur atom; and each bioactive moiety is a group selected from the list consisting of a group which can function as a metabolic substrate, catalyst or inhibitor; a group which can preferentially be taken up at a selected biological site; a group which contains reactive groups for coupling to a protein; or a group which can preferentially localize at a selected biological site.

4. A kit comprising a pharmaceutically acceptable reducing agent and a compound of the following formula:

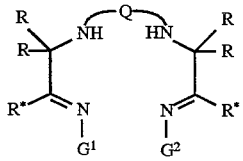

where Q is the group —$(C(RR))_{m1}$—$(Y^1)_n$—$(C(RR))_{m2}$—$(Y^2)$—$(C(RR))_{m3})_{n1}$—, where $Y^1$ and $Y^2$ are each independently —NR—, —O—, —S—, —SO—, —$SO_2$— or —Se—; n and n1 are each independently 0 or 1; and m1, m2 and m3 are each independently 0 or an integer from 1 to 4; provided that m1 and m2 are not both 0, that m1+m2+n+n1 is less than 6 and that a carbon atom bearing an R group is not directly bonded to more than one heteroatom; each R and R* group is independently:

(i) $R^1$;
(ii) alkoxy;
(iii) hydroxy;
(iv) halogen;
(v) haloalkyl;
(vi) —$OR^1$;
(vii) —C(O)—$OR^1$;
(viii) —C(O)—$N(R^1)_2$;
(ix) —$N(R^1)_2$—;
(x) —$N(R^1)$—$COR^1$;
(xi) —alkyl—C(O)—$OR^1$;
(xii) —alkyl—C(O)—$N(R^1)_2$;
(xiii) —alkyl—$N(R^1)$;
(xiv) —alkyl—$N(R^1)$—$COR^1$;
(xv) —aryl—C(O)—$OR^1$;
(xvi) —aryl—C(O)—$N(R^1)_2$;
(xvii) —aryl—$N(R^1)_2$;
(xviii) —aryl—$N(R^1)$—$COR^1$;
(xix) nitrile;
(xx) acyl;
(xxi) acyloxy;
(xxii) heterocyclo;
(xxiii) hydroxyalkyl;
(xxiv) alkoxyalkyl;
(xxv) hydroxyaryl;
(xxvi) arylalkyl;
(xxvii) —$SO_2$—$R^1$;
(xxviii) —alkyl—$SO_2$—$R^1$;
(xxix) —$(A)_p$—$R^a$, where A is a linking group which is bound to $R^a$ via a carbon, oxygen, nitrogen or sulfur group, p is 0 or a positive integer, and $R^a$ is a bioactive moiety or a reactive group which forms a covalent bond to a bioactive moiety; or (xxx) two of the groups, taken together with one or more atoms to which they are bonded, form a saturated or unsaturated, spiro or fused, carbocyclic or heterocyclic ring which may be unsubstituted or substituted by one or more groups selected from the groups (i) to (xxix) above;

each $R^1$ is independently hydrogen, alkyl, alkenyl, alkynyl or aryl; and $G^1$ and $G^2$ are each independently —OH or —$N(R^2)_2$, provided that at least one of $G^1$ and $G^2$ is —$N(R^2)_2$, where each $R^2$ is independently hydrogen, alkyl, aryl, acyl or —$(A)_p$—$R^a$;

each alkyl is substituted or unsubstituted and has 1 to 12 carbon atoms;

each alkoxy is substituted or unsubstituted and has 1 to 12 carbon atoms;

each alkenyl is substituted or unsubstituted and has 2 to 10 carbon atoms;

each alkynyl is substituted or unsubstituted and has 2 to 10 carbon atoms;

each cycloalkyl is substituted or unsubstituted and is a 1- to 3-ring system where each ring contains 3 to 7 carbon atoms;

each aryl is substituted or unsubstituted and is a homocyclic aromatic group which contains 1 or 2 rings where each ring contains 6 to 12 carbon atoms;

each heterocyclo is substituted or unsubstituted and is a saturated or unsaturated, aromatic or non-aromatic cyclic group containing at least one oxygen, nitrogen or sulfur atom; and each bioactive moiety is a group selected from the list consisting of a group which can function as a metabolic substrate, catalyst or inhibitor; a group which can preferentially be taken up at a selected biological site; a group which contains reactive groups for coupling to a protein; or a group which can preferentially localize at a selected biological site.

5. The kit of claim 4 wherein said kit comprises a single vial containing said compound and said reducing agent.

6. A kit comprising first and second vials, where said first vial contains a pharmaceutically acceptable reducing agent and said second vial contains a compound of the following formula:

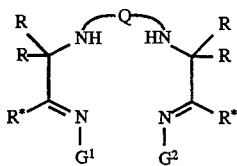

where Q is the group —(C(RR))$_{m1}$—(Y$^1$)$_n$—(C(RR))$_{m2}$—(Y$^2$—(C(RR))$_{m3}$)$_{n1}$—, where Y$^1$ and Y$^2$ are each independently —NR—, —O—, —S—, —SO—, —SO$_2$— or —Se—; n and n1 are each independently 0 or 1; and m1, m2 and m3 are each independently 0 or an integer from 1 to 4; provided that m1 and m2 are not both 0, that m1+m2+n+n1 is less than 6 and that a carbon atom bearing an R group is not directly bonded to more than one heteroatom; each R and R* group is independently:

(i) R$^1$;
(ii) alkoxy;
(iii) hydroxy;
(iv) halogen;
haloalkyl;
(vi) 1—OR$^1$;
(vii) —C(O)—OR$^1$;
(viii) —C(O) —N(R$^1$)$_2$;
(ix) —N(R$^1$)$_2$—;
(x) —N(R$^1$)—COR$^1$;
(xi) —alkyl—C(O)—OR$^1$;
(xii) —alkyl—C(O)—N(R$^1$)$_2$;
(xiii) —alkyl—N(R$^1$);
(xiv) —alkyl—N(R$^1$)—COR$^1$;
(xv) —aryl—C(O)—OR$^1$;
(xvi) —aryl—C(O)—N(R$^1$)$_2$;
(xvii) —aryl—N(R$^1$)$_2$;
(xviii) —aryl—N(R$^1$)—COR$^1$;
(xix) nitrile;
(xx) acyl;
(xxi) acyloxy;
(xxii) heterocyclo;
(xxiii) hydroxyalkyl;
(xxiv) alkoxyalkyl;
(xxv) hydroxyaryl;
(xxvi) arylalkyl;
(xxvii) —SO$_2$—R$^1$;
(xxviii) —alkyl—SO$_{2l-R}$$^1$;
(xxix) —(A)$_p$—R$^a$, where A is a linking group which is bound to R$^a$ via a carbon, oxygen, nitrogen or sulfur group, p is 0 or a positive integer, and R$^a$ is a bioactive moiety or a reactive group which forms a covalent bond to a bioactive moiety; or
(xxx) two of the groups, taken together with one or more atoms to which they are bonded, form a saturated or unsaturated, spiro or fused, carbocyclic or heterocyclic ring which may be unsubstituted or substituted by one or more groups selected from the groups (i) to (xxix) above;

each R$^1$ is independently hydrogen, alkyl, alkenyl, alkynyl or aryl; and

G$^1$ and G$^2$ are each independently —OH or —N(R$^2$)$_2$, provided that at least one of G$^1$ and G$^2$ is —N(R$_2$)$_2$, where each R$^2$ is independently hydrogen, alkyl, aryl, acyl or —(A)$_p$—R$^a$;

each alkyl is substituted or unsubstituted and has 1 to 12 carbon atoms;

each alkoxy is substituted or unsubstituted and has 1 to 12 carbon atoms;

each alkenyl is substituted or unsubstituted and has 2 to 10 carbon atoms;

each alkynyl is substituted or unsubstituted and has 2 to 10 carbon atoms;

each cycloalkyl is substituted or unsubstituted and is a 1- to 3-ring system where each ring contains 3 to 7 carbon atoms;

each aryl is substituted or unsubstituted and is a homocyclic aromatic group which contains 1 or 2 rings where each ring contains 6 to 12 carbon atoms;

each heterocyclo is substituted or unsubstituted and is a saturated or unsaturated, aromatic or non-aromatic cyclic group containing at least one oxygen, nitrogen or sulfur atom; and each bioactive moiety is a group selected from the list consisting of a group which can function as a metabolic substrate, catalyst or inhibitor; a group which can preferentially be taken up at a selected biological site; a group which contains reactive groups for coupling to a protein; or a group which can preferentially localize at a selected biological site.

\* \* \* \* \*